United States Patent
Masino et al.

(10) Patent No.: US 10,324,015 B2
(45) Date of Patent: Jun. 18, 2019

(54) VISCOSITY SENSOR

(71) Applicants: Halliburton Energy Services, Inc., Houston, TX (US); James Masino, Houston, TX (US); Li Gao, Katy, TX (US)

(72) Inventors: James Masino, Houston, TX (US); Li Gao, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 224 days.

(21) Appl. No.: 15/108,644

(22) PCT Filed: Mar. 25, 2014

(86) PCT No.: PCT/US2014/031745
§ 371 (c)(1),
(2) Date: Jun. 28, 2016

(87) PCT Pub. No.: WO2015/147803
PCT Pub. Date: Oct. 1, 2015

(65) Prior Publication Data
US 2016/0327465 A1    Nov. 10, 2016

(51) Int. Cl.
*E21B 49/08* (2006.01)
*G01N 11/16* (2006.01)

(52) U.S. Cl.
CPC ............ *G01N 11/167* (2013.01); *E21B 49/08* (2013.01); *G01N 11/16* (2013.01); *E21B 2049/085* (2013.01)

(58) Field of Classification Search
CPC ...... G01N 11/16; G01N 11/08; G01N 11/142; G01N 2009/006; G01N 2011/002;
(Continued)

(56) References Cited

U.S. PATENT DOCUMENTS

| | | | |
|---|---|---|---|
| 5,103,679 A | * | 4/1992 | Porter .................. G01N 33/445 73/54.39 |
| 2004/0255648 A1 | * | 12/2004 | Sparks .................. G01F 1/8404 73/54.41 |

(Continued)

FOREIGN PATENT DOCUMENTS

WO    2013173495 A1    11/2013

OTHER PUBLICATIONS

International Preliminary Examining Authority, International Preliminary Report on Patentability, International application No. PCT/US14/31745, which is a PCT parent to the instant application, dated May 31, 2016.

(Continued)

*Primary Examiner* — Randy W Gibson
*Assistant Examiner* — Gedeon M Kidanu
(74) *Attorney, Agent, or Firm* — Howard L. Speight, PLLC

(57) ABSTRACT

A fluid is received into a sample tube. A processor causes an energy to be applied to the sample tube to induce vibration in the sample tube at a resonant frequency of the sample tube containing the fluid. The processor stops the supply of energy to the sample tube. The processor monitors an amplitude of the vibration of the sample tube as the amplitude of the vibrations diminish over a period of time. The processor uses the monitored amplitude to calculate an $R_F$ of the sample tube containing the fluid. The processor uses the calculated $R_F$ to calculate the viscosity of the fluid.

13 Claims, 12 Drawing Sheets

(58) Field of Classification Search
CPC ... G01N 2291/021; G01N 2291/02818; G01N 29/036; G01N 29/222; G01N 29/227; G01N 29/46; G01N 33/28; G01N 33/2888; G01N 33/445
See application file for complete search history.

(56) References Cited

U.S. PATENT DOCUMENTS

| | | | | |
|---|---|---|---|---|
| 2005/0087001 | A1* | 4/2005 | Irani | G01N 11/08 73/54.04 |
| 2011/0167910 | A1* | 7/2011 | Storm | G01F 1/74 73/32 A |
| 2014/0151457 | A1* | 6/2014 | Wilkerson | H01L 41/042 239/4 |
| 2016/0108729 | A1* | 4/2016 | Li | G01N 11/16 702/12 |

OTHER PUBLICATIONS

International Searching Authority, International Search Report and Written Opinion, International application No. PCT/US2014/031745, which is a PCT parent of the instant application, dated Oct. 17, 2014.
Visual Physics School of Physics University of Sydney Australia, Fluid Flow Viscosity Poiseuille's Law.

* cited by examiner

VISCOSITY SENSOR

BACKGROUND

Measuring viscosity is useful in a variety of contexts including, but not limited to, drilling wells, where a viscosity measurement can be used to distinguish fluids in a borehole.

DETAILED DESCRIPTION

Figure 1:
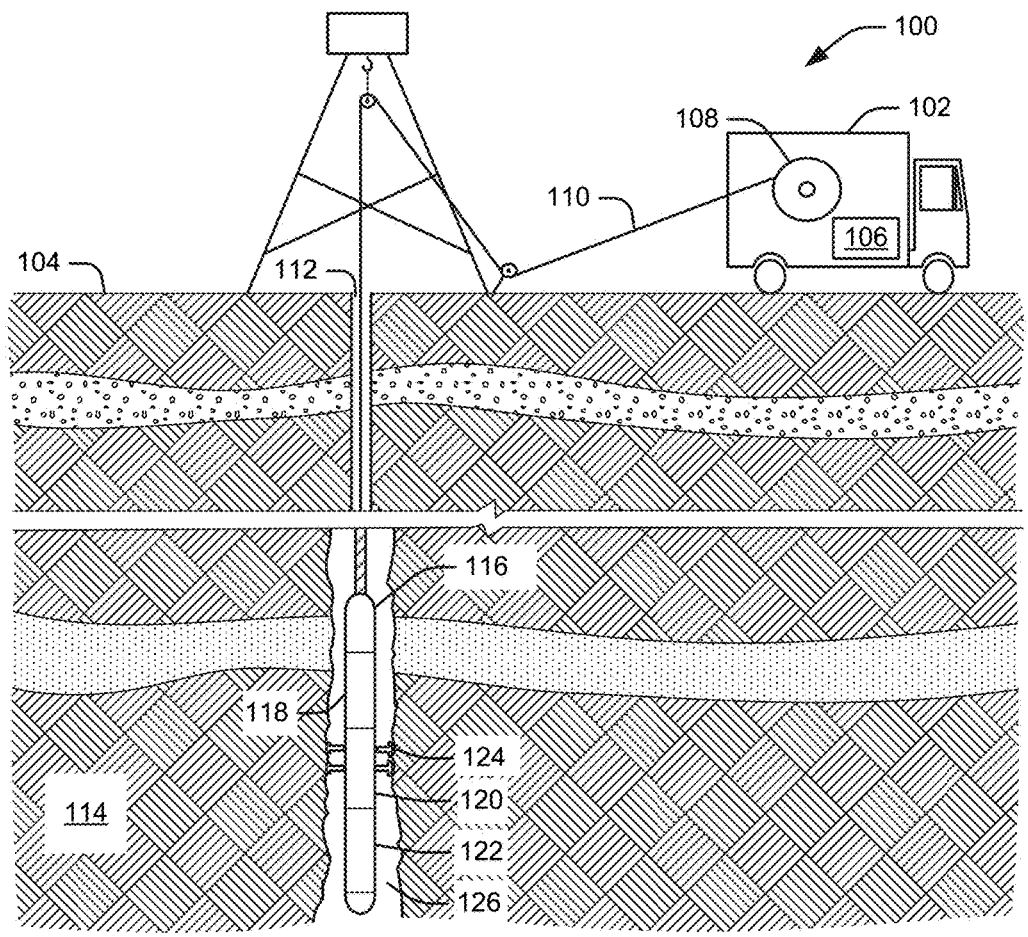
FIG. 1 shows a wireline system.

In one embodiment of a wireline or slickline well logging system 100 (greatly simplified for illustration) at a well site, as depicted in FIG. 1, a logging truck or skid 102 on the earth's surface 104 houses a data gathering system 106 and a winch 108 from which a cable 110 extends into a borehole 112 to a sub-surface formation 114. In one embodiment, the cable 110 suspends a logging toolstring 116 within the borehole 112 to measure formation data as the logging toolstring 116 is raised or lowered by the wireline 110. In one embodiment, the logging toolstring 116 includes a first downhole logging tool 118, a second downhole logging tool 120, and a third downhole logging tool 122. In one embodiment, the second downhole logging tool 120 is a formation testing tool to collect data about fluid extracted from subsurface formations, such as formation 114. While FIG. 1 shows a land-based wireline system, the equipment and techniques described herein are also useful in a sea-based wireline system and in land and sea based drilling systems and slickline systems.

In one embodiment, the data gathering system 106 receives data from the downhole logging tools 118, 120, 122 and sends commands to the downhole logging tools 118, 120, 122. In one embodiment the data gathering system 106 includes input/output devices, memory, storage, and network communication equipment, including equipment necessary to connect to the Internet (not shown in FIG. 1).

Figure 2:
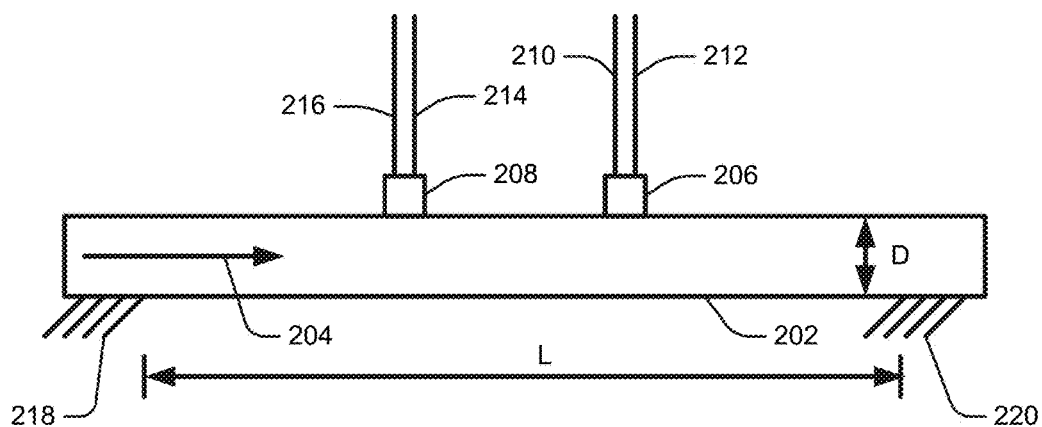
FIG. 2 shows a schematic of a sample tube.

In one embodiment, illustrated in FIG. 2, the formation testing tool 120 includes a sample tube 202. In one embodiment, the sample tube 202 is constructed of metal, glass, or a ceramic material. In one embodiment, a fluid (i.e., a liquid or a gas) to be tested, represented by arrow 204, flows through the sample tube 202. In one embodiment, the fluid to be tested 204 is extracted from the formation 114 through a probe or plunger 124 (shown in FIG. 1) that is part of formation testing tool 120, routed through valves and tubing (not shown) in the formation testing tool 120, and directed through the sample tube 202. In one embodiment, the fluid to be tested 204 is ejected into the annulus 126 (i.e., the annular portion of the borehole 112 surrounding the logging toolstring 116, see FIG. 1) after passing through the sample tube 202. In one embodiment, the fluid to be tested 204 is stored in sample chambers (not shown) for further testing.

In one embodiment, a transmitter 206 imparts energy to the sample tube 202, causing it to vibrate. In one embodiment, a receiver 208 detects vibrations in the sample tube 202. The transmitter 206 and the receiver 208 have respective leads 210, 212, 214, 216 through which signals are routed.

Viscosity is a resistance to flow caused by friction between molecules in a fluid. Such resistance occurs at the interface between a fluid and its container, such as between the fluid to be tested 204 and the inner surface of the sample tube 202 shown in FIG. 2. The apparatus shown in FIG. 2 can be used to measure viscosity and density of the fluid to be tested.

Figure 3:
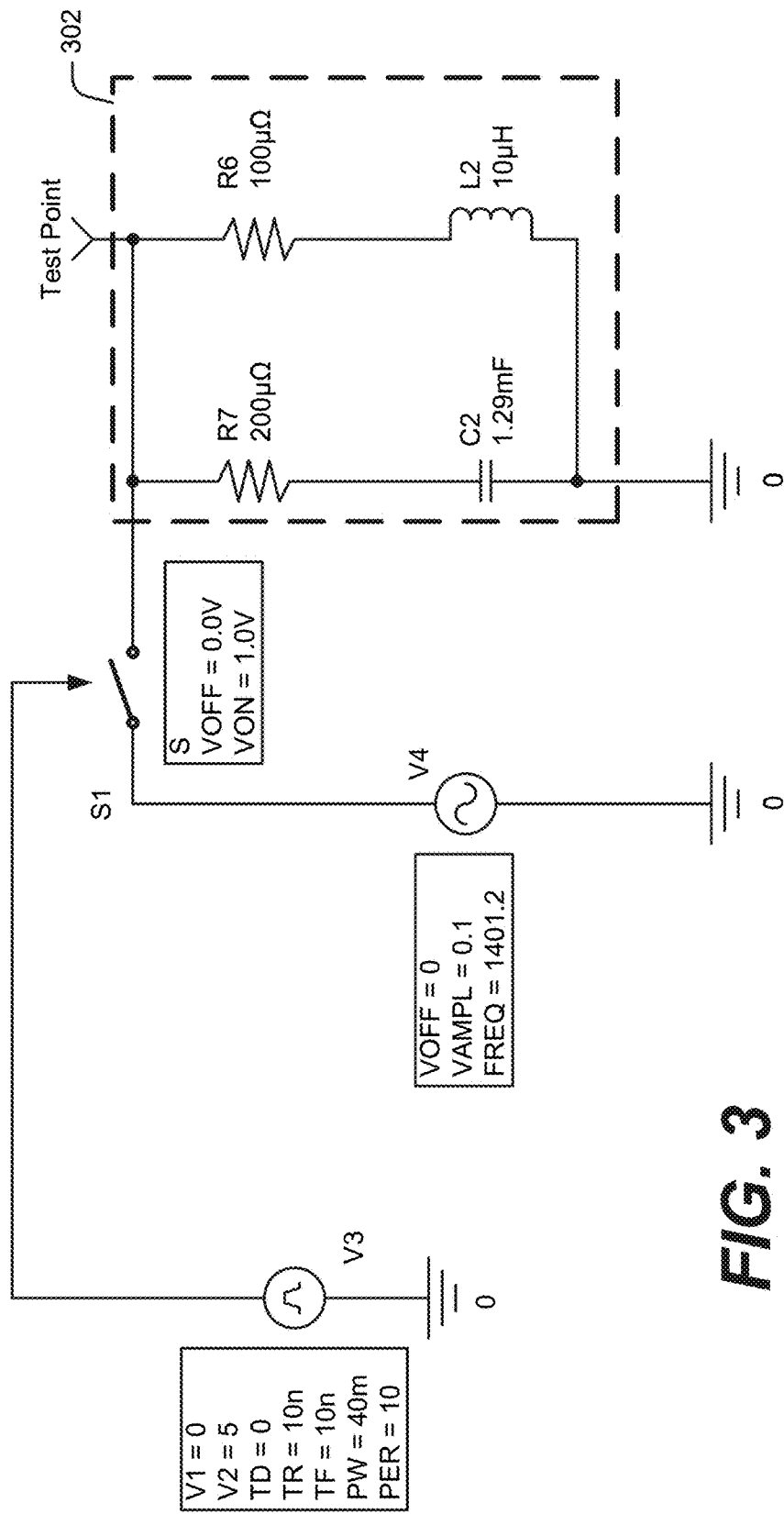
FIG. 3 shows a schematic of an electrical analogy for a distributed mass and spring representation of a sample tube and components for exciting the electrical analogy into oscillation.

In one embodiment, the sample tube 202 is a distributed mass and spring arrangement, which is modeled by the electrical circuit analogy shown in FIG. 3. In this model, capacitor C2 represents a mass, inductor L2 represents a spring, R7 represents the lossy real (i.e., non-imaginary) part of the capacitor C2, and R6 represents the lossy real part of the inductor L2. C2, L2, R7 and R6 form a resonant circuit 302. The other components in FIG. 3 are described below.

For a vibrating tube, such as the sample tube 202 when stimulated by the transmitter 206, a resonant frequency occurs when distributed complex impedances of opposite magnitudes precisely cancel one another, or, in other words, when:

$$|-jXC| = |+jXL| \tag{1}$$

where:

$$j = \sqrt{-1},$$

XC is the magnitude of the impedance of the capacitive analogy of the sample tube, and XL is the magnitude of the impedance of the inductive analogy of the sample tube.

The imaginary impedances $-jXC$ and $+jXL$ are accompanied by respective real resistances $R_C$ and $R_L$, such as those discussed above in connection with FIG. 3, that account for energy loss due to friction. In one embodiment, the real resistances in the sample tube 202 at resonance are represented by $R_T$, which is a combination of all resonant circuit energy losses in varying proportions due to electrical and mechanical interactions, including but not limited to:

material friction of the vibrating sample tube 202 itself, be it metal, glass, or ceramic;

coils and circuit resistances that sustain sample tube 202 oscillation;

friction of gas outside the sample tube 202, and friction of gas or fluid inside the sample tube 202.

In one embodiment, these resistances are separated into two groups: $R_F$, which is defined as friction due to gas or fluid inside the sample tube 202, and $R_O$, which is defined as all other frictions:

$$\text{i.e., } R_O = R_T - R_F \text{ or } R_T = R_O + R_F \tag{2}$$

In one embodiment, for a resonant circuit, $R_T$ is calculated using equation (3):

$$R_T = \frac{X}{Q} \quad (3)$$

where
X is XL or XC, and $$Q = \frac{f_{resonant}}{BW}, \quad (4)$$

$f_{resonant}$ is the resonant frequency of the resonant circuit, $BW = f_{High} - f_{Low}$ $f_{High}$ is a frequency greater than the resonant frequency at which the response of the resonant circuit is 50 percent of the power amplitude of vibration at the resonant frequency, and $f_{Low}$ is a frequency less than the resonant frequency at which the response of the resonant circuit is 50 percent of the power amplitude of vibration at the resonant frequency.

In one embodiment, in the case of a vibrating tube, such as sample tube 202, X represents the reactive distributed mass or spring characteristics of the tube.

The mass of sample tube 202 varies as a function of its content (i.e., whether the sample tube 202 has fluid flowing through it and what fluid is flowing through it) but, when empty, its mass is constant over a large temperature range. In one embodiment the mass of the portion of the sample tube 202 between the anchors 218 and 220 is determined by conventional means using a balance or a weight scale. In the case where a weight scale is used the gravitational acceleration is used to convert the measurement to mass. To reiterate, the mass of the sample tube 202 is constant when the sample tube 202 is empty. In contrast, the spring characteristic of the sample tube 202 varies as a function of temperature and pressure within the sample tube 202. In one embodiment, using the analogy that L corresponds to 1/k, with k being the spring constant of the sample tube 202, and C corresponds to m, i.e., the mass of empty sample tube 202, a function XL(temperature, pressure) is calculated using the equation $XL = 2\pi L f_{resonant}$ over a range of temperatures and pressures, where $f_{resonant}$ is measured, L is calculated using the equation $$L = \frac{1}{C(2\pi f_{resonant})^2},$$

and C is known over the range of temperatures and pressure. In one embodiment, a calibration process is used to generate XL(temperature, pressure) over the range of temperatures and pressures. In one embodiment, the range of temperatures is 10° to 205° Centigrade and the range of pressures is 0 to 30,000 pounds per square inch. In one embodiment, the function XL(temperature, pressure) is stored in a lookup table. In one embodiment, Q of the empty sample tube 202 is measured and equation (3) is used to calculate $R_T$, which is equal to $R_O$ because the sample tube 202 is empty (i.e., $R_F = 0$ when there is no fluid flowing through the sample tube 202). $R_O$ does not change when fluid flows through the sample tube 202. In one embodiment, the calibration procedure is performed for each formation testing tool 120.

Subsequently, in one embodiment, with fluid flowing through the sample tube 202, Q is calculated using one of the techniques described below, the appropriate value of the previously determined XL(temperature, pressure) and the calculated Q are substituted into equation (3) to calculate $R_T$ and equation (2) is used to calculate $R_F$. Further, in one embodiment, the fluid mass, Cfluid, is computed using the following equation:

$$C_{fluid} = \frac{1}{XL(\text{temperature, pressure})\sqrt{2\pi f_{resonant}}} - C,$$

where C is the mass of the flow tube 202 when it is empty (determined as described above), XL(temperature, pressure) is retrieved from the lookup table described above, and $f_{resonant}$ is the measured resonant frequency.

In one embodiment, viscosity of the fluid flowing through the sample tube 202, i.e., fluid to be tested 204, is calculated using the following formula, which is derived from an electrical analog of Poiseulle's Law:

$$u = \frac{\pi D^4 R_F}{128 L} \quad (5)$$

where
u is viscosity,
D is the inside diameter of the sample tube 202 (see FIG. 2), and
L is the active length of the sample tube 202 (i.e., the portion of the sample tube 202 undergoing vibration, e.g., the distance between anchors 218 and 220 (see FIG. 2, in which the symbols used are not intended to imply a mechanical design or implementation)).

In one embodiment, L>>D (e.g., L>10D, L>20D, or L>50D).

In one embodiment, Q is calculated using the ring-down time of the sample tube 202. This embodiment is discussed in connection with the model shown in FIG. 3, which is provided only for the purpose of illustrating the Q-calculation technique discussed below. In one embodiment, the components shown in FIG. 3 are not actually present in implementations but are useful in describing operation. In one embodiment, a single-pole single-throw switch S1 is controlled by a power source V3. In one embodiment, power source V3 has two states. In one embodiment, in the first state, the output of V3 is V1 (0 volts in the example shown). In one embodiment, in the second state, the output of V3 is V2 (5 volts in the sample shown). In one embodiment, the rise time between V1 and V2 is TR (10 nanoseconds (ns) in the example shown), the fall time between V2 and V1 is TF (10 ns in the example shown), the pulse width is PW (40 m in the example shown), and the per-cycle is PER (10 seconds in the example shown). In one embodiment, when V3 is in its first state, the switch S1 is open. In one embodiment, when V3 is in its second state, the switch S1 is closed.

In one embodiment, switch S1 begins in its closed state (i.e., V3 is in its second state), and the output of a tunable energy source V4 is connected to the resonant circuit 302 at the junction of resistor R7 and resistor R6. In one embodiment, tunable energy source V4 is adjustable in frequency and voltage output. In one embodiment, using the analogy of FIG. 3, the tunable energy source V4 is coupled to the leads 210 and 212 of the transmitter 206 (see FIG. 2) so that energy is coupled from the tunable energy source V4 to the sample tube 202.

The resonant frequency of the RLC circuit 302 shown in FIG. 3, which includes resistors R7 and R6, capacitor C2, and inductor L2, is:

$$F_{resonant} = \frac{1}{2\pi\sqrt{L2*C2}} \quad (6)$$

In the example shown in FIG. 3, R7=200 μΩ (micro-Ohms), R6=100 μΩ, C2=1.29 mF (milli Farads), and L2=10 mH (micro Henrys). Applying equation (5), the resonant frequency of the RLC circuit 302 shown in FIG. 3 is 1401.2 Hz. In one embodiment, V4 is tuned to 1401.2 Hz to cause the sample tube 202 to vibrate at its resonant frequency.

Figures 4, 5:
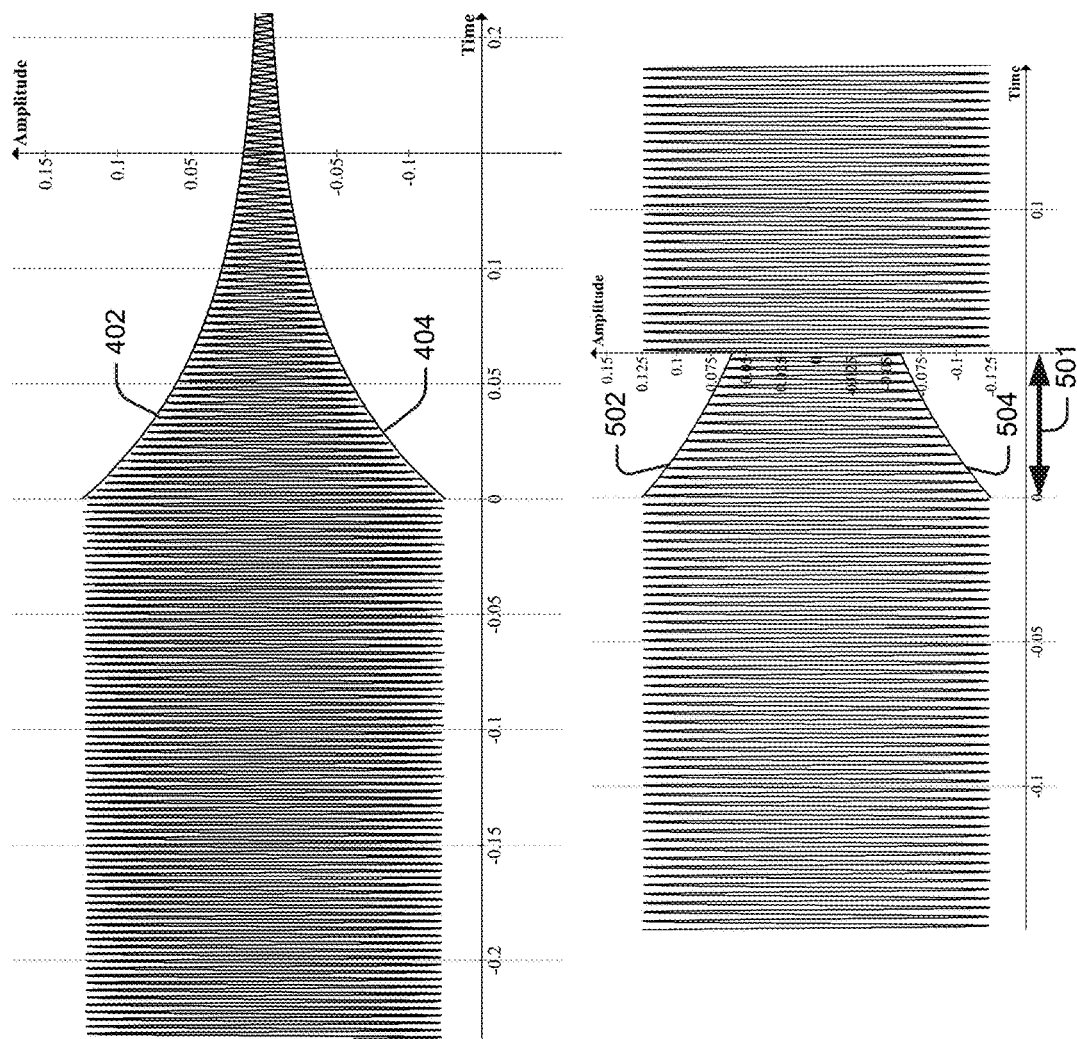
FIGS. 4 and 5 show the ring-down of oscillations of a sample tube.

In one embodiment, power source V3 is switched at time t=0 from its V1 state to its V2 state causing switch S1 to be opened, which interrupts the application of energy to the sample tube 202 represented by the resonant circuit 302 in FIG. 3. In one embodiment, the interruption of application of energy to the sample tube 202 is achieved by zeroing the input signal of the amplifier driving transmitter 206 at leads 210 and 212. One embodiment of the resulting vibration of the sample tube 202, as detected by the negative receiver 208 and the positive receiver 210, illustrated in FIG. 4, shows the vibration decaying over time.

In one embodiment, the transmitter 206 (see FIG. 2) performs the functions of tunable energy source V4. In one embodiment, a controller (not shown) causes the transmitter 206 to start and stop transmitting, thereby performing the functions of power source V3 and switch S1.

For illustration purposes, the equation for the vibration of the sample tube 202 before V3 is switched to its open position is:

$$A \sin(\omega t) \quad (7)$$

where
A is the amplitude of the vibration (0.125 in the example shown in FIG. 4),
ω is the frequency of the vibration (8804 radians/second (1401.2 Hz×2π) in the example, although another frequency was used in creating FIG. 4 so that the sinusoidal nature of the vibration could be illustrated), and
t is time.

The equation for vibration of the sample tube 202 after V3 is switched at time t=0 is:

$$A \sin(\omega t)e^{-\tau t} \quad (8)$$

where
τ is a decay constant (14.68 in the example shown in FIG. 4).

The vibration illustrated in FIG. 4 can be seen to have an upper envelope signal 402:

$$Ae^{-\tau*dt} \quad (9)$$

and a lower envelope signal 404:

$$-Ae^{-\tau*dt} \quad (10)$$

In one embodiment, root-mean-square ("RMS") envelopes are used in which the expressions of equations (9) and (10) are multiplied by $$\frac{\sqrt{2}}{2}(\sim 0.707).$$

In one embodiment, an RMS envelope detector (not shown) is provided that measures the RMS envelope.

In one embodiment, Q is determined by measuring the time ($d_{t37\%}$) it takes for one of the envelope signals to decay to $100*e^{-1}$ percent (referred to hereinafter, for simplicity, as "37 percent") of its maximum value. While 37 percent of its maximum value was chosen for computational simplicity, as shown below, any point on the decay curve (i.e., the 10 percent point, the 25 percent point, or the 50 percent point) could be used as long as the computation is revised accordingly. An alternative representation of Q is:

$$Q = \frac{\pi f_{resonant}}{\tau} \quad (11)$$

When the magnitude of the envelope is 37 percent of its maximum value:

$$\frac{Envelope_{37\%}}{Envelope_{max}} = e^{-\tau*dt_{37\%}} = .37 \quad (12)$$

Where
$Envelope_{max}$ is the maximum value of the envelope signal, and
$Envelope_{37\%}$ is the value of the envelope signal at 37 percent of its maximum.

Taking the natural logarithm of both sides of equation (12) (this computation demonstrates the computational simplicity of using "37 percent of its maximum"):

$$-\tau*dt_{37\%}=-1 \quad (13)$$

Therefore, $$\tau=1/dt_{37\%} \quad (14)$$

Substituting equation (14) into equation (11) yields:

$$Q=dt_{37\%}*f_{resonant}*\tau \quad (15)$$

In one embodiment, once Q is known, the procedure to calculate viscosity described above is followed.

In one embodiment, it is desired to limit the ring-down time illustrated in FIG. 4 to avoid impacting on-going measurements of fluid density which use continuous vibration of the sample tube 202, especially where the value of Q is high causing the ring-down to 37 percent of maximum to require more than 50 milliseconds. For example, in FIG. 4, the ring-down to 37 percent of maximum takes 68.12 milliseconds (ms) ($dt_{37\%}=1/\tau=1/14.68$). In some cases, waiting for the vibration to ring down to the 37 percent point is inconvenient.

Figure 6:
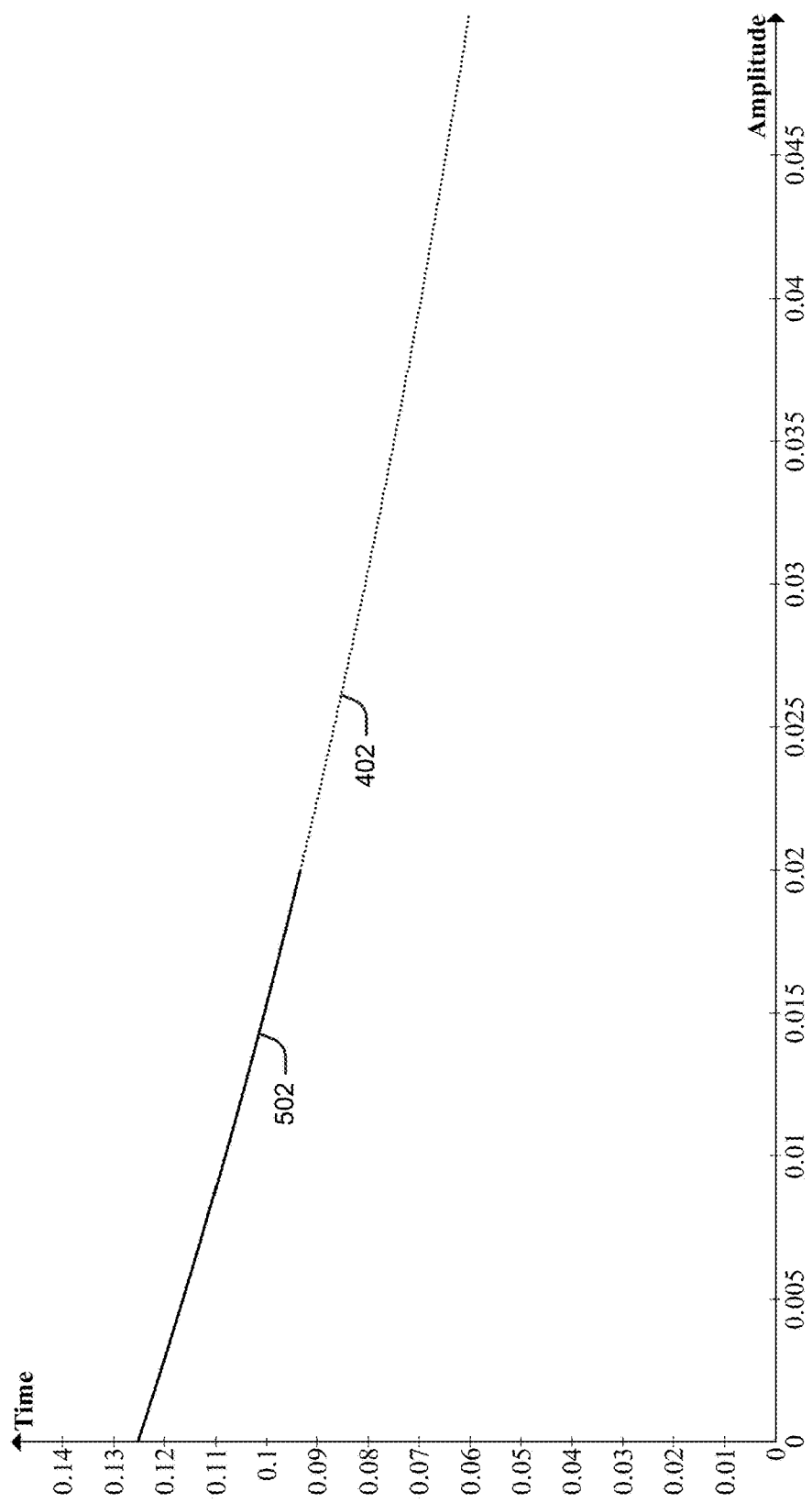
FIG. 6 shows portions of envelopes of ring-down oscillations of a sample tube.

In one embodiment, illustrated in FIG. 5, the ring-down time 501 is limited to a particular value. In the example of FIG. 5, the ring-down time 501 is limited to less than 50 ms to give time for computation and telemetry. In one embodiment, FIG. 5 shows two envelopes, a shortened upper envelope 502, which, in one embodiment, is a portion of upper envelope 402, and a shortened lower envelope 504, which, in one embodiment, is a portion of lower envelope 404. In one embodiment, RMS envelopes are used. FIG. 6 shows the relationship between shortened upper envelop 502 and upper envelop 402. A similar relationship exists between the shortened lower envelop 504 and the lower envelop 404.

In one embodiment, $dt_{37\%}$ is estimated using either or both of the shortened upper envelope 502 and the shortened lower envelope 504. In one embodiment, samples of one or both of the shortened upper envelope 502 and the shortened lower envelope 504 are taken. The samples from one or both of the envelopes are fit to a decay curve to produce:

$$V(t) = A_{max} e^{-\tau * t} \quad (16)$$

where $A_{max}$ and $\tau$ are discovered by curve fitting, and $V(t)$ is the upper envelope 402 or the lower envelope 404. It will be understood that the analysis described below could be done for an RMS version of the envelope 404. It will further be understood that the same analysis could be done if peak samples were taken and peak envelopes were developed.

In one embodiment, the curve fitting is done using as few as two points, one of the points being the time at which the ring-down begins. In one embodiment, the curve fitting is done with many more points. In one embodiment, the curve fitting is done with more than 50 points. In one embodiment, the curve fitting is done with more than 500 points. In one embodiment, the curve fitting is done with more than 5000 points.

Using the inverse of equation (14):

$$dt_{37\%} = 1/\tau \quad (17)$$

Substituting equation (17) into equation (15) yields equation (11). In one example, $\tau = 14.68$, and $f_{resonant} = 1401.2$, yielding $Q = 299.86$.

In an alternative embodiment, Q is measured by modifying the circuitry that sustains oscillation in the sample tube 202. In particular, in one embodiment, a variable delay circuit is inserted in the closed-loop-circuit that sustains oscillation in the sample tube 202. The variable delay circuit is controlled to force the sample tube 202 to vibrate slightly off its resonant peak causing a lower voltage to be observed on the leads 214 and 216 of the receiver 208. In one embodiment, by recording the output voltage of the receiver 208 as the excitation frequency is varied, Q can be calculated directly. That is, in one embodiment, BW is observed and $f_{resonant}$ is observed, allowing Q to be calculated directly using equation (4).

Figure 7:
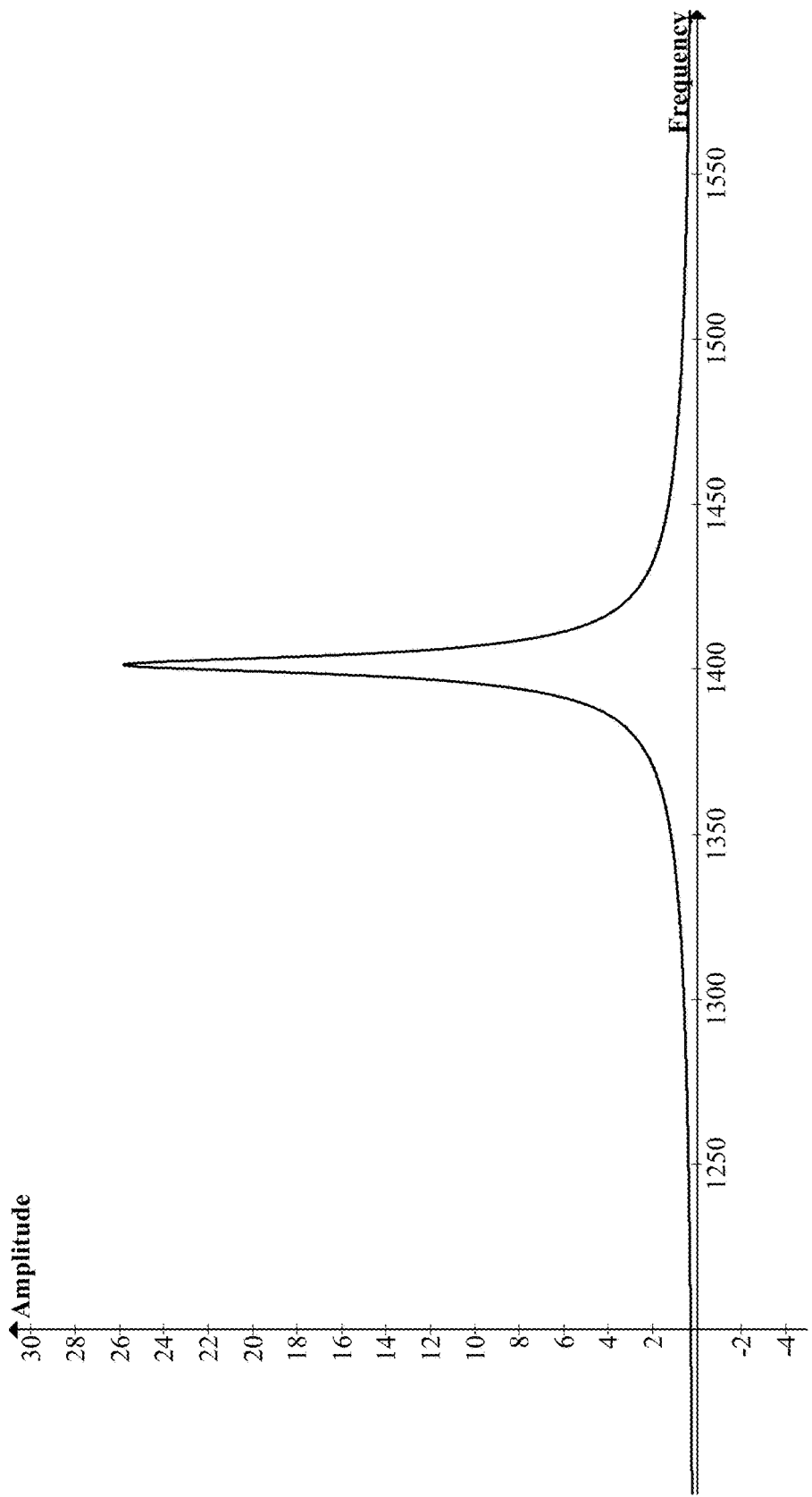
FIGS. 7 and 8 show the transfer function amplitude response of an electrical analogy to a simplified mass spring representation of a sample tube.

To illustrate, a graph of the transfer function H(s) of the resonant circuit 302 (see FIG. 3) is shown in FIG. 7. The transfer function has the following equation:

$$H(s) = \frac{V(s)}{i(s)} \quad (18)$$
$$= \frac{R7 * C2 * L2 * s^2 + R7 * C2 * R6 * s + L2 * s + R6}{C2 * L2 * s^2 + C2 * R7 * s + C2 * R6 * s + 1}$$

where

V(s) is the voltage measured relative to ground at the test point shown in FIG. 3 in the frequency domain, i(s) is the current flowing through the resonant circuit 302, $s = j\omega$, $\omega = 2\pi *$frequency, and R7, R6, C2, and L2 have the values described above in the discussion of FIG. 3.

The vertical "Amplitude" axis in FIG. 7 is the magnitude of H(s):

$$\text{Amplitude} = \sqrt{|H_i(s)|^2 + |H_r(s)|^2} \quad (19)$$

where:

$|H_i(s)|$ is the magnitude of the imaginary component of H(s), and $|H_r(s)|$ is the magnitude of the real component of H(s).

Figure 8:
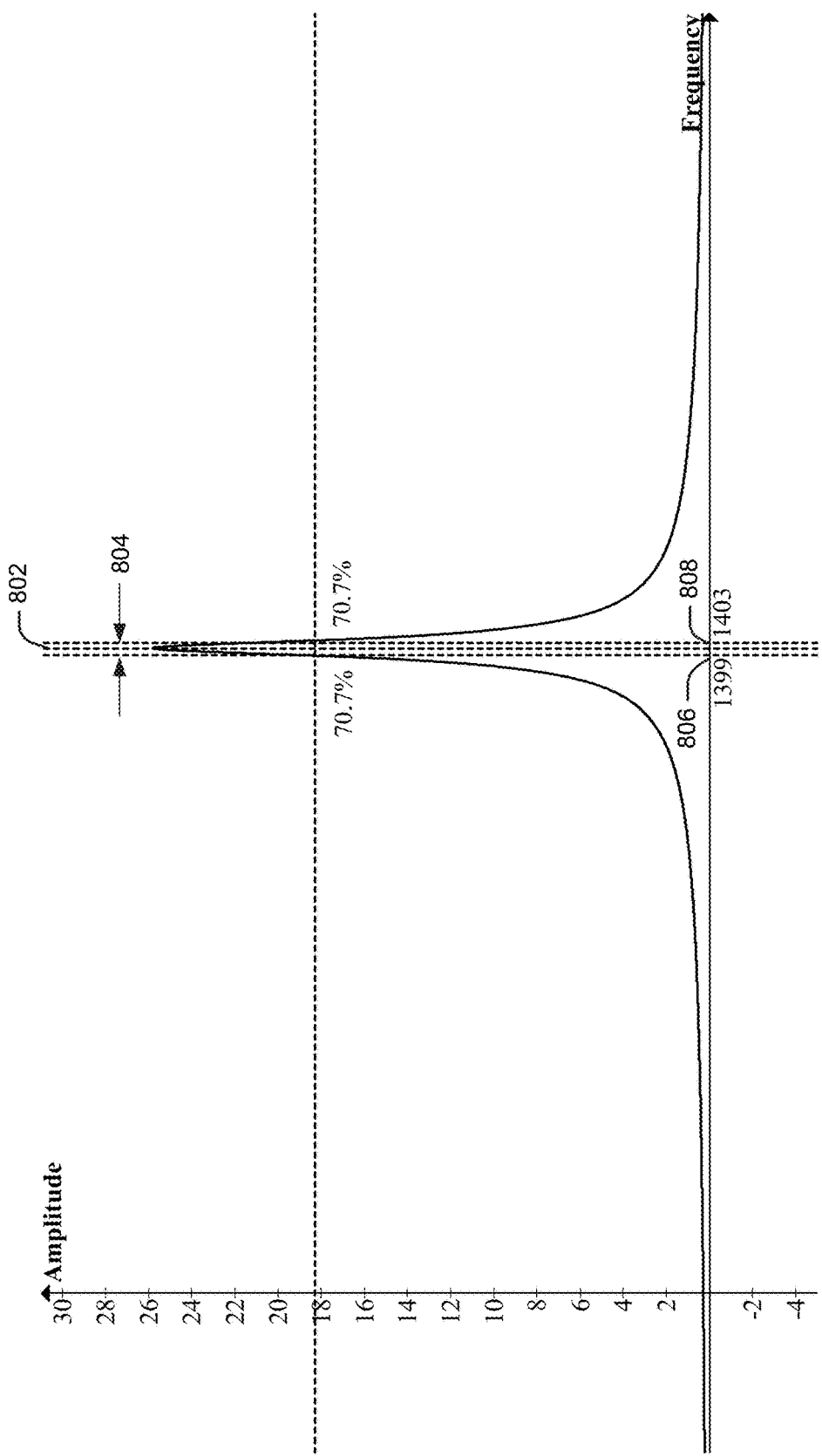
Figure 9:
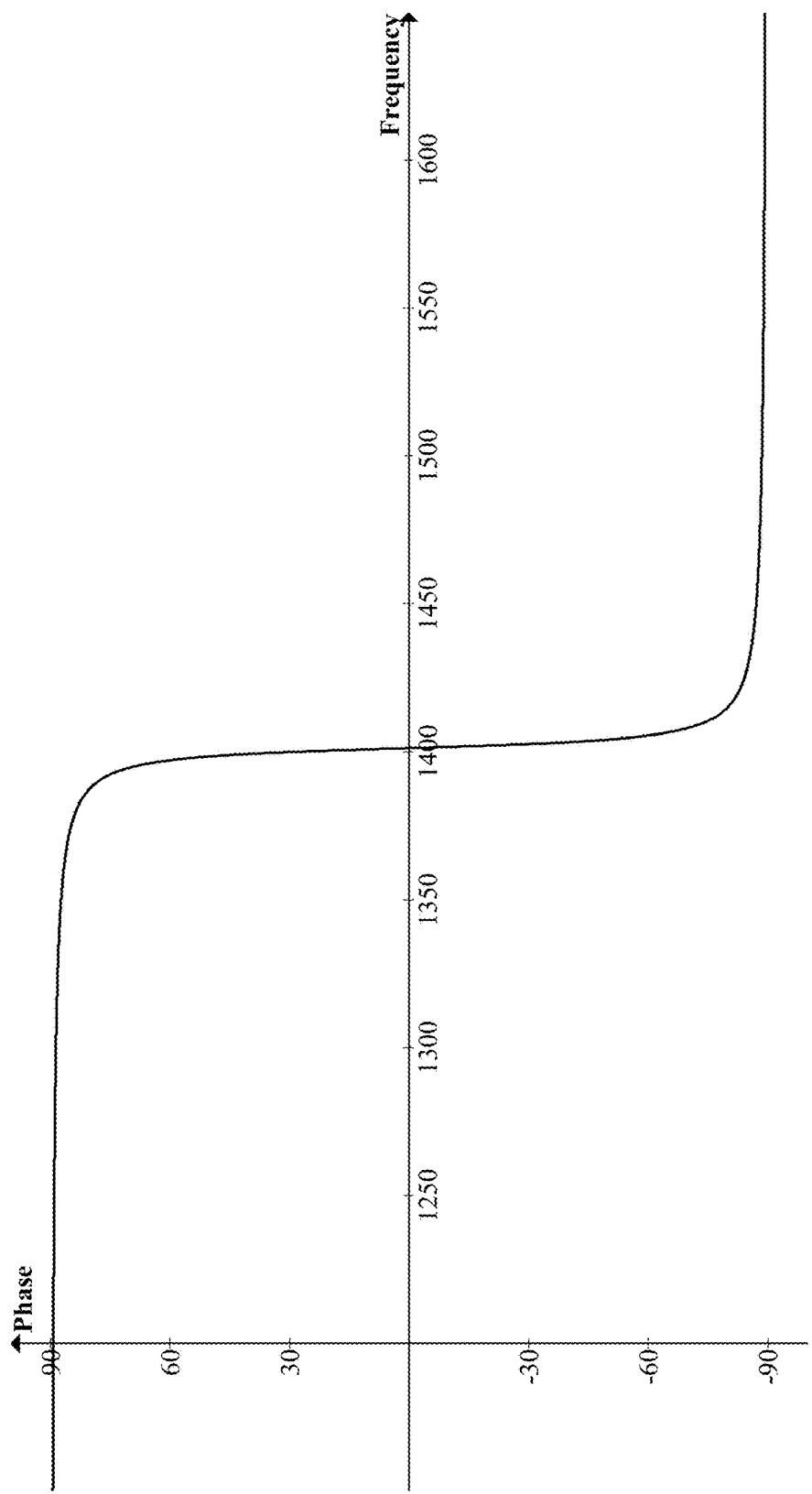
FIG. 9 shows the transfer function phase response of an electrical analogy to a simplified mass and spring representation of a sample tube.

The frequency of resonance, $f_{resonant}$, 802, and the bandwidth BW, 804, are illustrated for the same curve in FIG. 8. FIG. 9 illustrates the relationship between phase and frequency in H(s). The vertical "Phase" axis in FIG. 9 is the phase of H(s):

$$\text{Phase} = \text{atan}\left(\frac{|H_i(s)|}{|H_r(s)|}\right) \quad (20)$$

Figure 10:
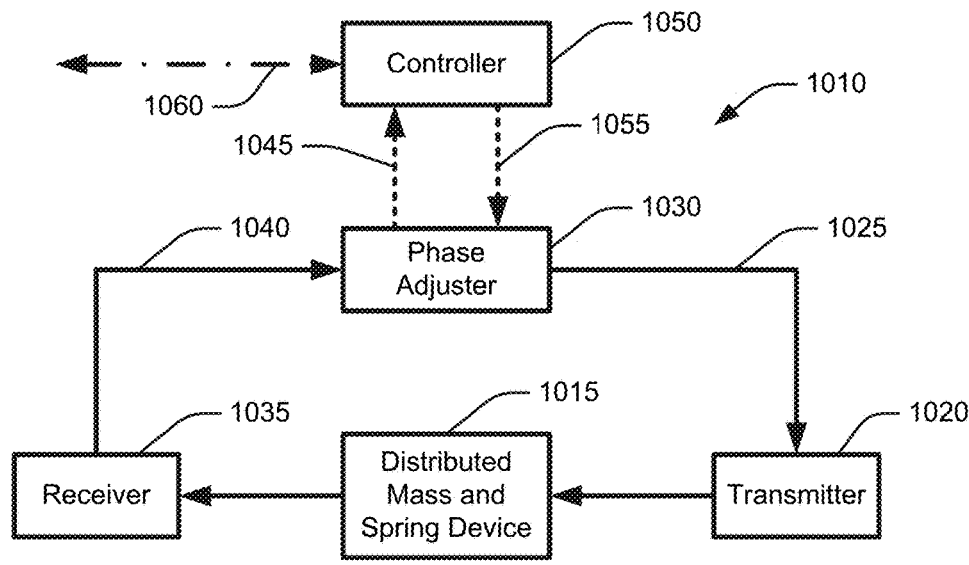
FIG. 10 is a block diagram of a viscosity sensor and its implementation.

One embodiment of a Q-measuring circuit 1010, illustrated in FIG. 10, includes a distributed mass and spring device 1015, i.e., a device that can be modeled as a distributed mass and spring, such as sample tube 202 (see FIG. 2), which can be represented in an electrical analog by resonant circuit 302 (see FIG. 3). In one embodiment, a transmitter 1020, such as transmitter 206 (see FIG. 2), receives a phase-adjuster signal 1025 from a phase adjuster 1030 and stimulates vibrations in the distributed mass and spring device 1015 that correspond to the phase-adjuster signal 1025. In one embodiment, a receiver 1035, such as receiver 208 (see FIG. 2), detects vibrations in the distributed mass and spring device 1015 and produces a corresponding vibration signal 1040.

In one embodiment, the phase adjuster 1030 receives the vibration signal 1040. In one embodiment, the phase adjuster 1030 provides a representation signal 1045, which is a representation of the vibration signal 1040, such as the magnitude of the vibration signal 1040 or the root-mean-square (RMS) magnitude of the vibration signal, to a controller 1050. In one embodiment, the controller 1050 processes the representation signal 1045, as discussed below, and provides a control signal 1055 to the phase adjuster 1030. In one embodiment, the phase adjuster 1030 adjusts the phase of the vibration signal 1040 in response to the control signal 1055 to produce the phase-adjuster signal 1025. In one embodiment, the phase adjuster 1030 includes an inverter, as discussed below. In one embodiment, the controller 1050 is remotely controlled, for example by data gathering system 106 via remote control channel 1060.

Figure 11:
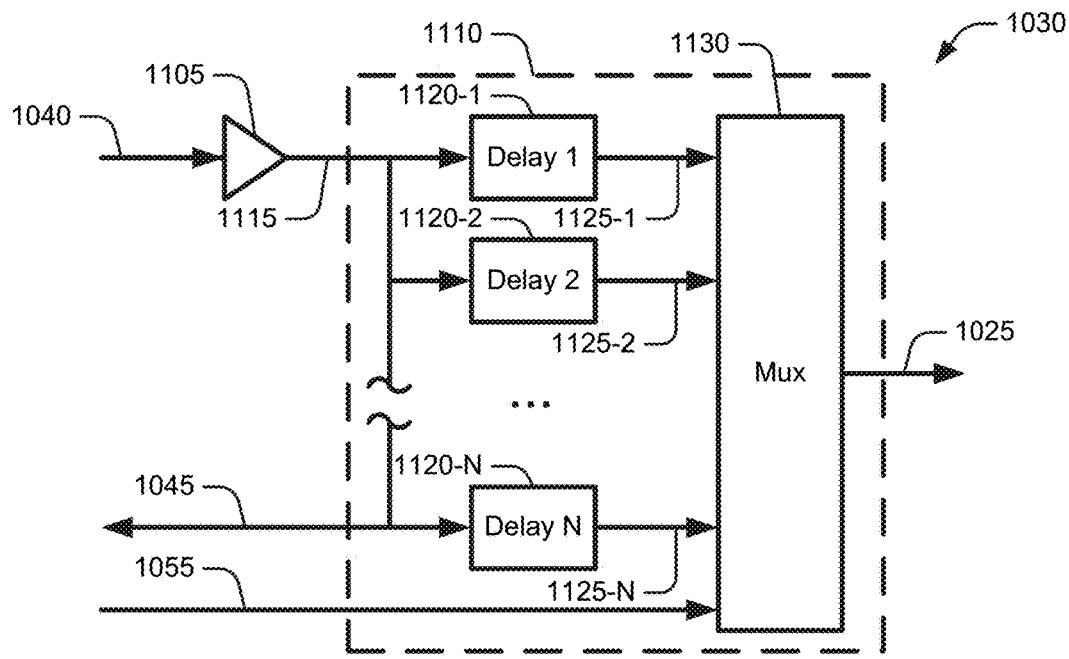
FIG. 11 is a block diagram of a phase adjuster.

In one embodiment, illustrated in FIG. 11, the phase adjuster 1030 includes a buffer 1105 and a phase delay circuit 1110. In one embodiment, the buffer 1105 is an amplifier that receives and amplifies the vibration signal 1040 so that if the vibration signal 1040 is positive the amplified signal is a digital "1" and if the vibration signal 1040 is negative the amplified signal is a digital "0." The buffer 1105 provides a buffered signal 1115 made up of the 1s and 0s to the phase delay circuit 1110. In one embodiment, the buffer 1105 has a gain of one so that the amplification operates as described immediately above. In one embodiment, the buffer 1105 is an inverter, i.e., with a gain of −1, so that if the vibration signal 1040 is positive the amplified signal is a digital "0" and if the vibration signal 1040 is negative the amplified signal is a digital "1." In one embodiment, the buffer 1105 has a high-impedance input and imposes little load on the output of the receiver 1035 that produces the vibration signal 1040. In one embodiment, the buffer 1105 is not present and the phase delay circuit 1110 provides a high-impedance input to the vibration signal 1040 and, if necessary, performs the inversion described above.

In one embodiment, the buffered signal 1115 is provided to the controller 1050 as the representation signal 1045. In one embodiment, the phase adjuster 1030 includes a circuit (not shown) that produces an RMS envelope of the buffered signal 1115 or the vibration signal 1040 and that signal is provided to the controller 1050 as the representation signal 1045.

One embodiment of the phase delay circuit 1110 is illustrated in FIG. 11. In one embodiment, the phase delay circuit 1110 includes N delay circuits all of which receive the buffered signal 1115 (or the vibration signal 1040 if the buffer 1105 is not present):

delay circuit 1 1120-1, which delays the buffered signal 1115 (or the vibration signal 1040 if the buffer 1105 is not present) by δ1 seconds to produce delayed signal 1125-1, delay circuit 2 1120-2, which delays the buffered signal 1115 (or the vibration signal 1040 if the buffer 1105 is not present) by δ2 seconds to produce delayed signal 1125-2, delay circuit 3 through delay circuit N−1 (represented by the ellipsis in FIG. 11), which delays the buffered signal 1115 (or the vibration signal 1040 if the buffer 1105 is not present) by δ3 through δN seconds, respectively, to produce delayed signals 1125-3 through 1125-N−1, and delay circuit N 1120-N, which delays the buffered signal 1115 (or the vibration signal 1040 if the buffer 1105 is not present) by δN seconds to produce delayed signal 1125-N.

In one embodiment, a multiplexer 1130 selects one of the delayed signals 1125-1 through 1125-N to appear at the output of the multiplexer 1130 and to be transmitted as the phase-adjuster signal 1025 according to a selection made by the control signal 1055. In one embodiment, the control signal follows a binary protocol so that, for example, a "000" (transmitted serially or through parallel lines (not shown) making up the control signal 1055) would cause delayed signal 1125-1 to appear at the output of the multiplexer 1130.

In one embodiment, the phase-adjuster signal 1025 is the vibration signal 1040 inverted by the buffer 1105 (or by the phase delay circuit 1110 if the buffer 1105 is not present), delayed by a delay inherent in the hardware in the phase adjuster 1030 (such as the inherent delay in the buffer 1105, if it is present), further delayed by an amount determined the selection of delayed signal 1125-1 through 1125-N by the multiplexer 1130.

It will be understood that the phase delay circuit 1110 can be any analog or digital circuit that can change the phase of the buffered signal 1115 (or the vibration signal 1040 if the buffer 1105 is not present) under control of the controller 1050 using the control signal 1055. It can be a digital circuit, such as that shown in FIG. 11, an analog circuit (not shown), or a mixture of digital and analog circuitry.

Further, the number of delay circuits 1120-1 through 1120-N can be larger or smaller than that shown in FIG. 11. In one embodiment, N is 8. In one embodiment, N is 32. In one embodiment, N is greater than 64.

Still further, the phase delay circuit 1110 can be a microprocessor or a microcontroller, with the phase delay process and perhaps the inversion being done by software or firmware.

Figure 12:
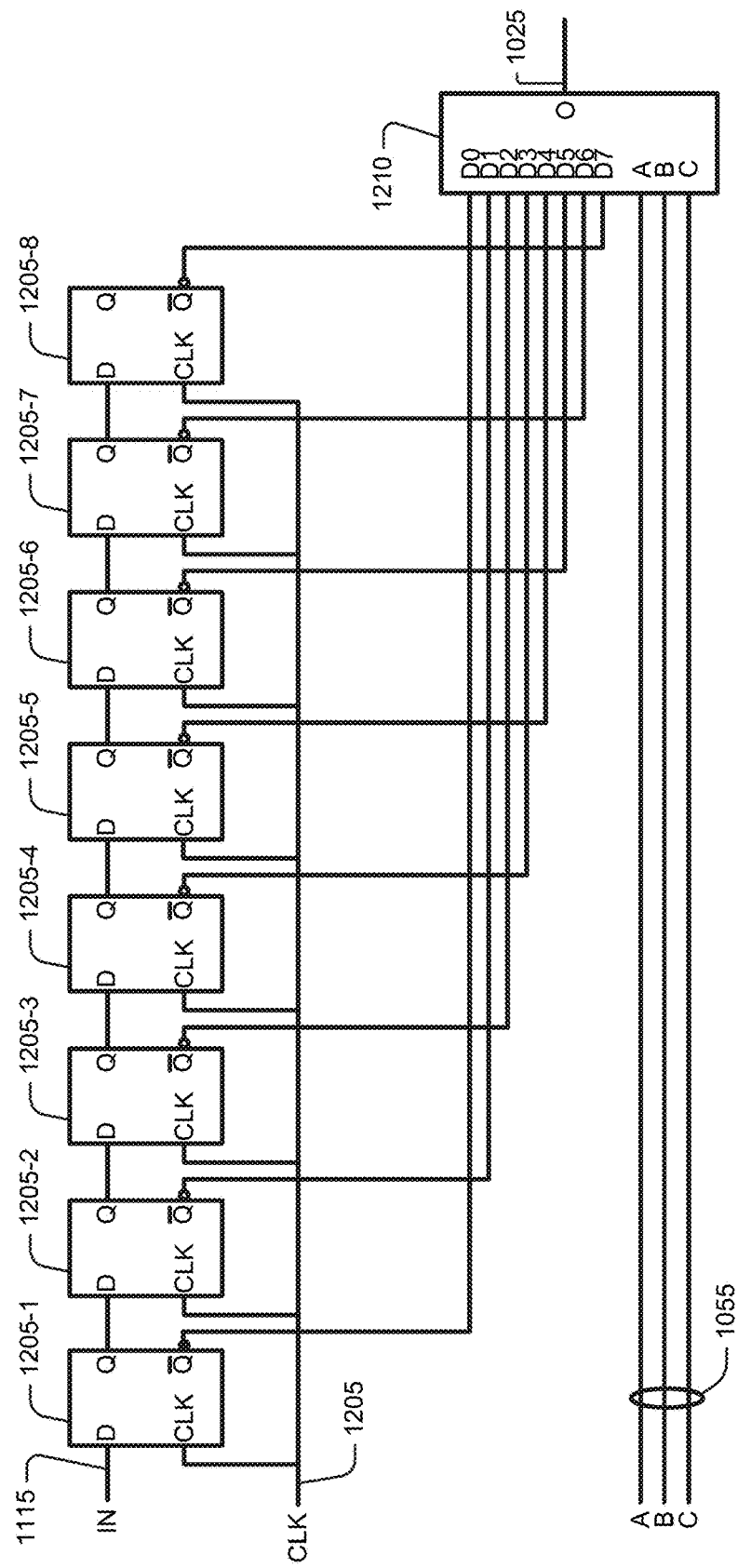
FIG. 12 is a block diagram of a phase delay circuit.

One embodiment of an example phase delay circuit 1110, illustrated in FIG. 12, includes an input that receives the output of the buffer 1115 and three signal lines that receive the control signal 1055. In one embodiment, a clock signal 1205 (not shown in FIG. 10) provides timing for the circuit.

In one embodiment, the delays are provided by daisy-chained flip-flops 1205-1 through 1205-8. Each D-flip-flop 1205-1 through 1205-8 has a D input, a clock ("CLK") input, a Q output, and a Q-bar ($\overline{Q}$) output In one embodiment, the Q output of each flip-flop changes to the value of the D input when the D-flip-flop is clocked through the clock input. In one embodiment, the $\overline{Q}$ output is the inverse of the Q output.

In one embodiment, the Q output of each flip-flop is tied to the D input of the subsequent flip-flop. For example, the Q output of flip-flop 1205-1 is tied to the D input of flip-flop 1205-2, Q output of flip-flop 1205-2 is tied to the D input of flip-flop 1205-3, and so on. As a result, the Q and $\overline{Q}$ outputs of each flip-flop provide a successive one clock cycle delay for the buffered signal 1115.

In one embodiment, the Q-bar outputs of each of the flop-flops 1205-1 through 1205-8 are tied to respective data inputs of a multiplexer 1210. In particular, in one embodiment:

the $\overline{Q}$ output of flip-flop 1205-1 is tied to the D0 input on the multiplexer 1210, the $\overline{Q}$ output of flip-flop 1205-2 is tied to the D1 input on the multiplexer 1210, the $\overline{Q}$ output of flip-flop 1205-3 is tied to the D2 input on the multiplexer 1210, the $\overline{Q}$ output of flip-flop 1205-4 is tied to the D3 input on the multiplexer 1210, the $\overline{Q}$ output of flip-flop 1205-5 is tied to the D4 input on the multiplexer 1210, the $\overline{Q}$ output of flip-flop 1205-6 is tied to the D5 input on the multiplexer 1210, the $\overline{Q}$ output of flip-flop 1205-7 is tied to the D6 input on the multiplexer 1210, and the $\overline{Q}$ output of flip-flop 1205-8 is tied to the D7 input on the multiplexer 1210.

In one embodiment, the multiplexer 1210 has an output O that is tied to the phase-adjuster signal 1025 output from the phase adjuster 1030. In one embodiment, the output O of the multiplexer is set to the value of the input D0-D7 selected by the control signal 1055 on its inputs A, B, and C. For example, if A=B=C=0, the signal on the D0 input will appear on the multiplexer's output O. Thus, in one embodiment, by manipulating the control signal 1055, the controller 1050 can adjust the amount of delay in the phase adjuster 1030.

In one embodiment, the circuit shown in FIG. 12 inverts the buffered signal 1115. Consequently, the buffer 1105 is not an inverter.

Returning to FIG. 10, in one embodiment, the circuit shows two closed loops. An inner loop includes the phase adjuster 1030, the transmitter 1020, the distributed mass and spring device 1015, and the receiver 1035, all connected by solid lines in FIG. 10. An outer loop includes the inner loop and adds the connections (1045 and 1055, shown as dashed lines in FIG. 10) between the phase adjuster 1030 and the controller 1050. The connection between the controller 1050 and an external controller, such as data gathering system 106, via remote control channel 1060 could be considered another, outer-most loop.

While the phase adjuster 1030 is shown in FIG. 10 as located between the receiver 1035 and the transmitter 1020, in one embodiment it can be located anywhere in the inner loop. Additionally Receiver 1035, Transmitter 1020 and Phase Adjuster 1030 may be integrated or otherwise combined.

Consider the Q-measuring circuit 1010 and assume (1) the phase adjuster 1030 is adjusted by the controller 1050 to introduce zero delay, (2) the gain of buffer 1105 represents the entire gain of the circuit and is greater than positive 1, and (3) the transmitter 1020 is adjusted to stimulate the distributed mass and spring device 1015 at its resonant frequency, $f_{resonant}$. In that case, the inner loop (indicated by the solid lines in FIG. 10) will oscillate at $f_{resonant}$ because the gain is greater than 1 and positive.

Now, continuing to assume the phase adjuster 1030 is adjusted by the controller 1050 to introduce zero delay, assume that the gain of the buffer 1105 is inverted so that it is negative and its magnitude is greater than 1. In that case, the inner loop (indicated by the solid lines in FIG. 10) will no longer oscillate because feedback in the loop is no longer positive and no longer sustains oscillation.

Assume also that the signal input to the phase adjuster 1030 (the vibration signal in FIG. 10) is periodic (such as a sinusoid) having a wavelength λ. If the controller 1050 adjusts the delay of the phase adjuster 1030 to a delay of λ/2, the resulting phase-adjuster signal 1025 will be the same in phase and magnitude as the phase-adjuster signal 1025 before the buffer 1105 was inverted. That is, the inner loop (indicated by the solid lines in FIG. 10) will have the same transfer function with an un-inverted buffer 1105 and no delay as it would have with an inverted buffer 1105 and a λ/2 delay.

Further, by adjusting the delay of phase adjuster 1030 on either side of λ/2 it is possible to change the frequency away from $f_{resonant}$ and towards either the lower or upper bandwidth limit 806 or 808 of FIG. 8, respectively.

The inner loop (indicated by the solid lines in FIG. 10) oscillates at or very near the first fundamental resonant frequency of the tube 202 in FIG. 2, and does so when the tube is empty or fluid filled, over a large range of temperatures, when given a default phase adjuster value and is brought even closer to peak resonance by the second control loop of FIG. 10.

Figure 13:
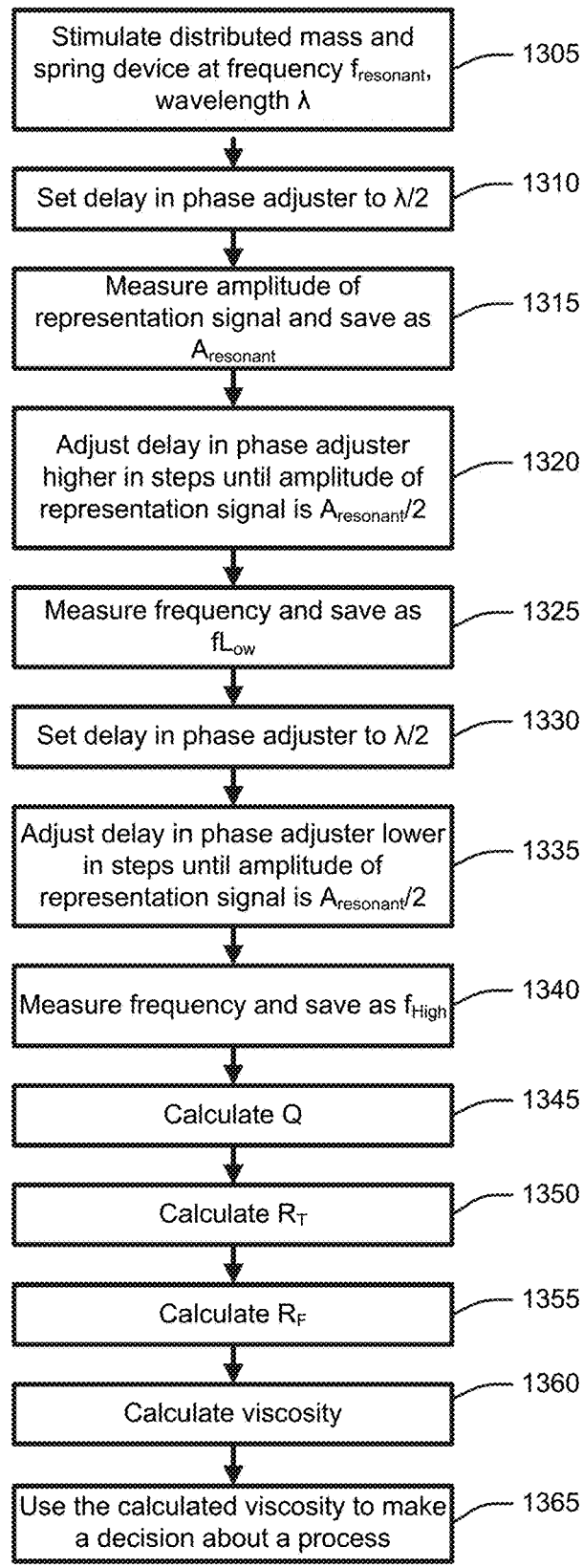
FIG. 13 is a flow chart.
Figure 14:
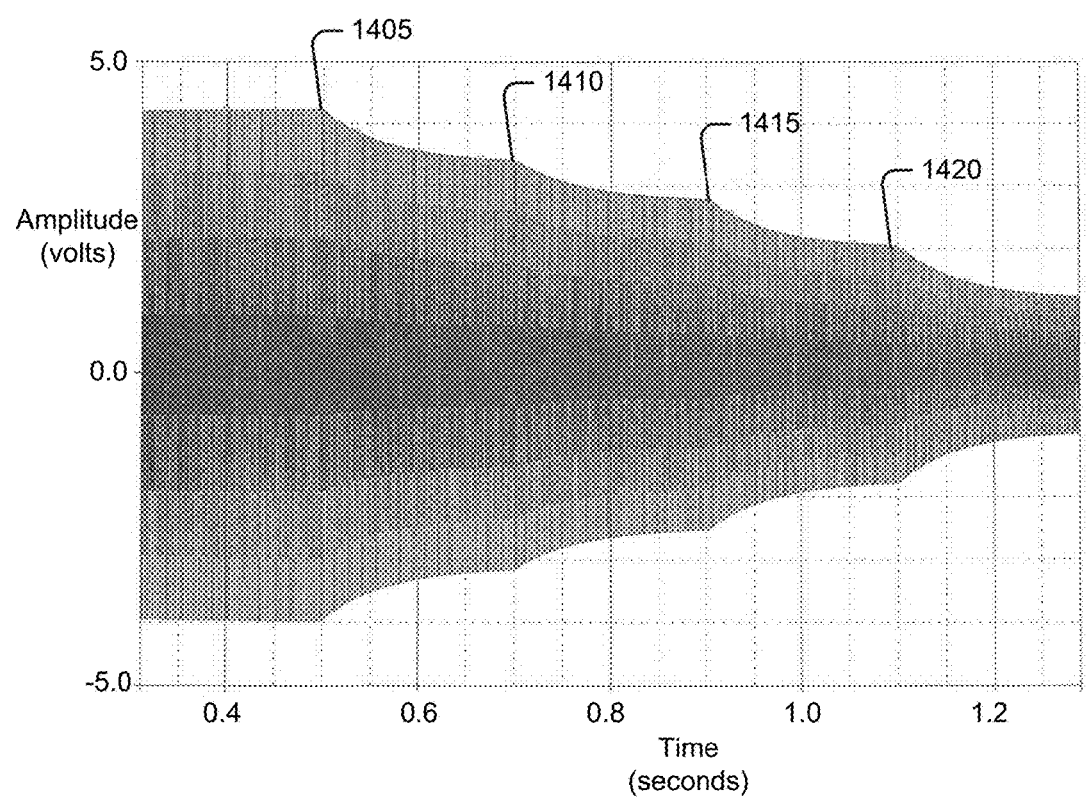
FIG. 14 illustrates a stepped decrease in the amplitude of vibrations of a sample tube as a result of tuning the vibrations away from the sample tube resonant frequency.

In one embodiment of use in which Q is calculated using equation (4), which means that $f_{High}$ and $f_{Low}$ are determined, as illustrated in FIG. 13 (the buffer 1105 is an inverting amplifier in this scenario):

transmitter 1020 stimulates the distributed mass and spring device 1015 at its first fundamental resonant frequency $f_{resonant}$ (block 1305)

the delay in the phase adjuster 1030 is set to λ/2 (block 1310), where λ is the wavelength of $f_{resonant}$, less any known delay in the hardware of the phase adjuster 1030, the amplitude of the representation signal 1045 is measured and saved as the $A_{resonant}$ (block 1315) (a conventional amplitude measuring device (not shown) is provided for this purpose), to determine $f_{Low}$, the delay in the phase adjuster 1030 is adjusted higher in steps, causing the frequency of oscillation of the inner loop (indicated by the solid lines in FIG. 10) to be reduced, until the amplitude of the representation signal 1045 is reduced to substantially (in one embodiment, within 1 percent; in one embodiment, within 5 percent; in one embodiment, within 10 percent) $A_{resonant}/2$ (block 1320) (the conventional amplitude measuring device (not shown) is used for this purpose) (FIG. 14 illustrates the reduction in amplitude of the representation signal 1045 as the frequency of oscillation is changed at times 1405, 1410, 1414, and 1420), the frequency of oscillation of the inner loop (indicated by the solid lines in FIG. 10) is measured and saved as $f_{Low}$ (block 1325), which is the low end 806 of the BW frequency range 804 as illustrated in FIG. 8 (the conventional frequency measuring device (not shown) is used for this purpose), the delay in the phase adjuster 1030 is set to λ/2 less any known delay in the hardware of the phase adjuster 1030 (block 1330), which resets the inner loop for determination of $f_{High}$, to determine $f_{High}$, the delay in the phase adjuster 1030 is adjusted lower in steps, causing the frequency of oscillation of the inner loop (indicated by the solid lines in FIG. 10) to be increased, until the amplitude of the representation signal 1045 is reduced to substantially (in one embodiment, within 1 percent; in one embodiment, within 5 percent; in one embodiment, within 10 percent) $A_{resonant}/2$ (block 1335)(the conventional amplitude measuring device (not shown) is used for this purpose), the frequency of oscillation of the inner loop (indicated by the solid lines in FIG. 10) is then measured and saved as $f_{High}$ (block 1340), which is the high end 808 of the BW frequency range 804 as illustrated in FIG. 8 (the conventional frequency measuring device (not shown) is provided for this purpose), Q is then calculated (block 1345) using equation (4) as:

$$Q = \frac{f_{resonant}}{f_{High} - f_{Low}} \qquad (21)$$

$R_T$ is calculated (block 1350) using equation (3),
$R_F$ is calculated (block 1355) using equation (2),
viscosity is calculated (block 1360) using equation (5), and
the calculated viscosity is used to make a decision about a process (block 1365).

In one example of using the calculated viscosity to make a decision about a process, the process is drilling a well, and a driller may decide that the fluids being produced from formation 114 are too viscous to be commercially valuable and decide not to produce from that formation. In another context, a fluid being developed in a chemical process may remain in one stage of production until its viscosity reaches a certain point at which time the chemical process proceeds to the next step.

In one embodiment, to avoid interference with density measurements being performed by the formation testing tool 120, which use continuous excitation at the resonant frequency of the sample tube 202 carrying a fluid 204, the delay circuit switches symmetrically to either side of the resonant frequency. This introduces a phase lag or a phase lead on either side of resonance; on average, the density measurement is unaffected. A varying resonant frequency is observed at the output of a density sensor (not shown) that allows BW to be measured.

In one embodiment, the curve shown in FIG. 7 is assumed to be symmetrical and only one of $f_{Low}$ and $f_{High}$ is measured. Q is then calculated using equation (27) (below) if only $f_{High}$ is measured (in which case blocks 1325, 1330, and 1335 need not be performed) and using equation (28) (below) if only $f_{Low}$ is measured (in which case blocks 1335, 1340, and 1345 need not be performed):

$$Q = \frac{f_{resonant}}{2(f_{High} - f_{resonant})} \qquad (27)$$

$$Q = \frac{f_{resonant}}{2(f_{resonant} - f_{low})} \quad (28)$$

A more general version of equations (27) and (28) is:

$$Q = \frac{f_{resonant}}{2|f_{resonant} - f_{half-BW}|} \quad (29)$$

where $f_{half-BW}$ is $f_{High}$ or $f_{Low}$, depending on which was measured.

Figure 15:
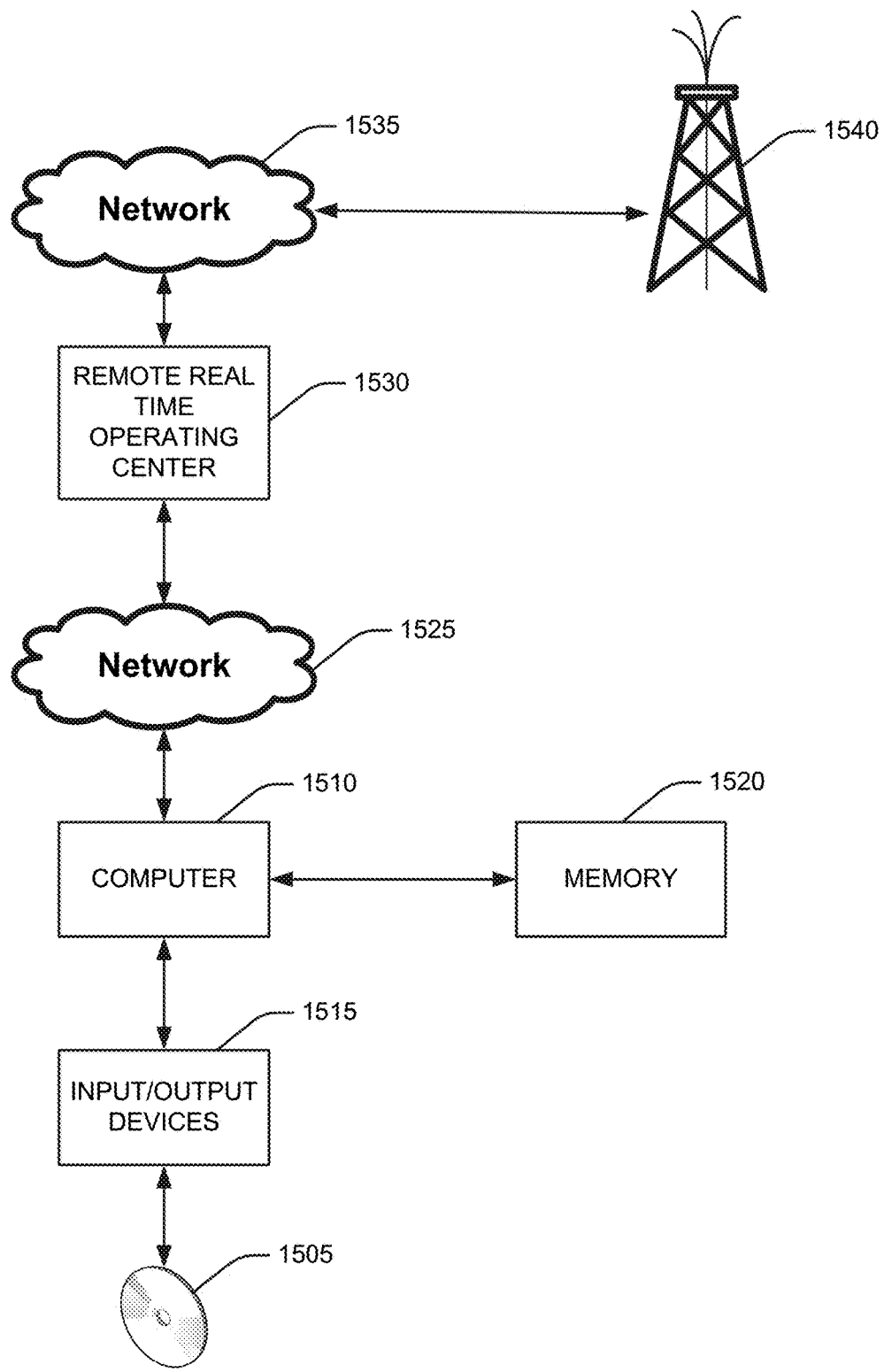
FIG. 15 illustrates an environment.

In one embodiment, shown in FIG. 15, the formation testing tool 120 (see FIG. 1) is controlled by software in the form of a computer program on a non-transitory computer readable media 1505, such as a CD, a DVD, a USB drive, a portable hard drive or other portable memory. In one embodiment, a processor 1510, which may be the same as or included in the controller 1050 or the data gathering system 106 (see FIG. 1), reads the computer program from the computer readable media 1505 through an input/output device 1515 and stores it in a memory 1520 where it is prepared for execution through compiling and linking, if necessary, and then executed. In one embodiment, the system accepts inputs through an input/output device 1515, such as a keyboard or keypad, mouse, touchpad, touch screen, etc., and provides outputs through an input/output device 1515, such as a monitor or printer. In one embodiment, the system stores the results of calculations in memory 1520 or modifies such calculations that already exist in memory 1520.

In one embodiment, the results of calculations that reside in memory 1520 are made available through a network 1525 to a remote real time operating center 1530. In one embodiment, the remote real time operating center 1530 makes the results of calculations available through a network 1535 to help in the planning of oil wells 1540 or in the drilling of oil wells 1540.

In general, in one aspect, the techniques described herein feature receiving a fluid into a sample tube. The techniques further feature a processor causing an energy to be applied to the sample tube to induce vibration in the sample tube at a resonant frequency of the sample tube containing the fluid. The techniques further feature the processor stopping the supply of energy to the sample tube. The techniques further feature the processor monitoring an amplitude of the vibration of the sample tube as the amplitude of the vibrations diminish over a period of time, using the monitored amplitude to calculate an $R_F$ of the sample tube containing the fluid, where $R_F$ is a friction due to fluid inside the sample tube, and using the calculated $R_F$ to calculate the viscosity of the fluid.

Embodiments may include one or more of the following, alone or in combination. The processor may cause the energy to be reapplied to the sample tube after a period of time. The processor may use the monitored amplitude to calculate the $R_F$ of the sample tube containing the fluid by using the amount of time required for the amplitude to diminish to a specified percentage of a maximum of the amplitude of the vibration of the sample tube to determine the $R_F$ of the sample tube containing the fluid. The specified percentage may be $100*e^{-1}$. The processor may use the monitored amplitude to calculate the $R_F$ of the sample tube containing the fluid by using amplitudes sampled and times elapsed at two times less than the amount of time required for the amplitude to diminish to a specified percentage of a maximum value of the amplitude of the vibration of the sample tube to estimate a specified-percentage time required for the amplitude to diminish to the specified percentage of the maximum value, and using the specified-percentage time to determine the $R_F$ of the sample tube containing the fluid. The period of time may be less than a time required for the amplitude to diminish to a specified percentage of a maximum value.

In general, in one aspect, the techniques described herein feature a processor determining the resonant amplitude of vibration of a sample tube through which a fluid is flowing when the sample tube through which the fluid is flowing vibrates at a resonant frequency $f_{resonant}$. The techniques further feature the processor determining a half-bandwidth frequency, $f_{half-BW}$, such that, when energy at the half-bandwidth frequency is applied to the sample tube through which the fluid is flowing, the sample tube through which the fluid is flowing vibrates at an amplitude substantially $$\frac{\sqrt{2}}{2}$$

times the resonant amplitude. The techniques further feature the processor calculating a calculated Q, calculating a friction resistance, $R_F$, using the calculated Q, and the processor calculating a viscosity of the fluid flowing through the sample tube, u, using $R_F$.

Embodiments may include one or more of the following, alone or in combination. The processor may determine the resonant amplitude of vibration of a sample tube through which the fluid is flowing when the sample tube through which the fluid is flowing is vibrated at a resonant frequency by finding the resonant frequency by adjusting a frequency of an excitation energy applied to the sample tube through which the fluid is flowing to maximize the resulting vibration. The processor may calculate the calculated Q by dividing $f_{resonant}$ by $2 \times |f_{resonant} - f_{half-BW}|$. $f_{half-BW}$ may be greater than $f_{resonant}$ and the processor may determine a lower-half-bandwidth frequency, $f_{Low}$, such that, when energy at $f_{Low}$ is applied to the sample tube through which the fluid is flowing, the sample tube through which the fluid is flowing vibrates at an amplitude substantially $$\frac{\sqrt{2}}{2}$$

times the resonant amplitude. The processor may calculate the calculated Q by dividing $f_{resonant}$ by $2*(f_{resonant} - f_{Low})$. The processor may calculate $R_F$ using the calculated Q by looking up XL (temperature, pressure) from a table using a temperature and a pressure of the sample tube through which the fluid is flowing, and calculating $R_F$ by dividing XL(temperature, pressure) by the calculated Q. The technique may further include creating the table by measuring XL at the resonant frequency of the sample tube in an empty state over a range of temperatures and a range of pressures. The technique may include the processor calculating u using $R_F$ by $$u = \frac{\pi D^4 R_F}{128 L}$$

where D is an inside diameter of the sample tube, and L is the length of the sample tube.

In general, in one aspect, the techniques described herein feature connecting the following components to form a closed loop: a distributed mass and spring device, a transmitter coupled to the distributed mass and spring device to stimulate the distributed mass and spring device to vibrate, a receiver coupled to the distributed mass and spring device to detect vibrations in the distributed mass and spring device containing a fluid, an inverter, and a phase adjuster comprising an adjustable delay. The techniques further feature the transmitter stimulating the distributed mass and spring device to vibrate at a resonant frequency, $f_{resonant}$, of the distributed mass and spring device, $f_{resonant}$ having a wavelength $\lambda$, setting the adjustable delay in the phase adjuster to $\lambda/2$, measuring the amplitude of the output of the receiver, $A_{resonant}$, when the distributed mass and spring device is vibrating at $f_{resonant}$, adjusting the adjustable delay in the phase adjuster away from $\lambda/2$ until the amplitude of the output of the $$\text{receiver} = \frac{\sqrt{2}}{2}$$

times $A_{resonant}$ and, in response, measuring the frequency of the output of the receiver, $f_{half-BW}$, calculating Q from $f_{resonant}$ and $f_{half-BW}$, and calculating a viscosity from Q.

Embodiments may include one or more of the following, alone or in combination. Connecting the components to form a closed loop may include connecting an input of the inverter to an output of the receiver, connecting an input of the phase adjuster to an output of the inverter, and connecting an output of the phase adjuster to an input of the transmitter. The techniques may further include measuring $f_{resonant}$ while measuring density using the distributed mass and spring device containing the fluid. Adjusting the adjustable delay in the phase adjuster may include increasing the adjustable delay. Calculating Q from $f_{resonant}$ and $f_{half-BW}$ may include calculating $$Q = \frac{f_{resonant}}{2 f_{half-BW}}.$$

Adjusting the adjustable delay in the phase adjuster may include increasing the adjustable delay and the techniques may further include setting the adjustable delay in the phase adjuster to $\lambda/2$, adjusting the adjustable delay in the phase adjuster away from $\lambda/2$ by decreasing the adjustable delay until the amplitude of the output of the $$\text{receiver} = \frac{\sqrt{2}}{2}$$

times $A_{resonant}$ and, in response, measuring the frequency of the output of the receiver, $f_{High}$, and calculating Q from $f_{resonant}$ and $f_{High}$. Q may be calculated using the following equation:

$$Q = \frac{f_{resonant}}{f_{High} - f_{resonant}}.$$

The distributed mass and spring device may include a sample tube. Calculating viscosity may include calculating $$R_T = \frac{X}{Q}$$

where X is XL or XC, XL is a magnitude of an inductive element of an electrical analog of the sample tube, and XC is a magnitude of an capacitive element of an electrical analog of the sample tube; calculating $R_F = R_T - R_O$, where $R_O$ is a previously-determined friction of the sample tube when it does not contain fluid; and calculating $$u = \frac{\pi D^4 R_F}{128 L}$$

where u is viscosity, D is the inside diameter of the sample tube, and L is the active length of the sample tube.

In general, in one aspect, the techniques described herein feature a computer program stored in a non-transitory computer readable storage medium. The program includes executable instructions that cause a processor to cause an energy to be applied to a sample tube containing a fluid to induce vibration in the sample tube at a resonant frequency of the sample tube containing the fluid, stop the supply of energy to the sample tube, monitor an amplitude of the vibration of the sample tube as the amplitude of the vibrations diminish over a period of time, use the monitored amplitude to calculate a $R_F$ of the sample tube containing the fluid, where $R_F$ is a friction due to fluid inside the sample tube, and use the calculated $R_F$ to calculate the viscosity of the fluid.

In general, in one aspect, the techniques described herein feature a computer program stored in a non-transitory computer readable storage medium. The program includes executable instructions that cause a processor to determine the resonant amplitude of vibration of a sample tube through which a fluid is flowing when the sample tube through which the fluid is flowing vibrates at a resonant frequency $f_{resonant}$, determine a half-bandwidth frequency, $f_{half-BW}$, such that, when energy at the half-bandwidth frequency is applied to the sample tube through which the fluid is flowing, the sample tube through which the fluid is flowing vibrates at an amplitude substantially $$\frac{\sqrt{2}}{2}$$

times the resonant amplitude, calculate a calculated Q, calculate a friction resistance, $R_F$, using the calculated Q, and calculate a viscosity of the fluid flowing through the sample tube, u, using $R_F$.

In general, in one aspect, the techniques described herein feature a computer program stored in a non-transitory computer readable storage medium. The program includes executable instructions that cause a processor to interact with the following components, which are connected to form a closed loop: a distributed mass and spring device, a transmitter coupled to the distributed mass and spring device to stimulate the distributed mass and spring device to vibrate, a receiver coupled to the distributed mass and spring device to detect vibrations in the distributed mass and spring device containing a fluid, an inverter, and a phase adjuster comprising an adjustable delay. The program further includes executable instructions that cause a processor to cause the transmitter to stimulate the distributed mass and spring device to vibrate at a resonant frequency, $f_{resonant}$, of the distributed mass and spring device, $f_{resonant}$ having a wavelength $\lambda$, set the adjustable delay in the phase adjuster to $\lambda/2$, measure the amplitude of the output of the receiver, $A_{resonant}$, when the distributed mass and spring device is vibrating at $f_{resonant}$, adjust the adjustable delay in the phase adjuster away from $\lambda/2$ until the amplitude of the $$receiver = \frac{\sqrt{2}}{2}$$

times $A_{resonant}$ and, in response, measure the frequency of the output of the receiver, $f_{half-BW}$, calculate Q from $f_{resonant}$ and $f_{half-BW}$, and calculate a viscosity from Q.

In general, in one aspect, the techniques described herein feature a closed loop circuit including a distributed mass and spring device, a transmitter coupled to the distributed mass and spring device to stimulate the distributed mass and spring device to vibrate, a receiver coupled to the distributed mass and spring device to detect vibrations in the distributed mass and spring device, an inverter, and a phase adjuster comprising an adjustable delay. The techniques further feature a controller coupled to the phase adjuster to control the adjustable delay.

Embodiments may include one or more of the following, alone or in combination. An input of the inverter may be coupled to an output of the receiver. An input of the phase adjuster may be coupled to an output of the inverter. An output of the phase adjuster may be coupled to an input of the transmitter. The distributed mass and spring device may include a sample tube.

The word "coupled" herein means a direct connection or an indirect connection.

The text above describes one or more specific embodiments of a broader invention. The invention also is carried out in a variety of alternate embodiments and thus is not limited to those described here. The foregoing description of an embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A method comprising:
    connecting components to form a closed loop, the components including:
        a distributed mass and spring device,
        a transmitter coupled to the distributed mass and spring device to stimulate the distributed mass and spring device to vibrate,
        a receiver coupled to the distributed mass and spring device to detect vibrations in the distributed mass and spring device containing a fluid,
        an inverter, and
        a phase adjuster comprising an adjustable delay;
    the transmitter stimulating the distributed mass and spring device to vibrate at a resonant frequency, $f_{resonant}$, of the distributed mass and spring device, $f_{resonant}$ having a wavelength $\lambda$;
    setting the adjustable delay in the phase adjuster to $\lambda/2$;
    measuring the amplitude of the output of the receiver, $A_{resonant}$, when the distributed mass and spring device is vibrating at $f_{resonant}$;
    adjusting the adjustable delay in the phase adjuster away from $\lambda/2$ until the amplitude of the output of the $$receiver = \frac{\sqrt{2}}{2}$$

times $A_{resonant}$ and, in response, measuring the frequency of the output of the receiver, $f_{half-BW}$;
    a processor calculating Q from $f_{resonant}$ and $f_{half-BW}$; and
    the processor calculating a viscosity from Q.

2. The method of claim 1 wherein connecting the components to form a closed loop comprises connecting an input of the inverter to an output of the receiver, connecting an input of the phase adjuster to an output of the inverter, and connecting an output of the phase adjuster to an input of the transmitter.

3. The method of claim 1 further comprising:
    measuring $f_{resonant}$ while measuring density using the distributed mass and spring device containing the fluid.

4. The method of claim 1 wherein adjusting the adjustable delay in the phase adjuster comprises increasing the adjustable delay.

5. The method of claim 1 wherein calculating Q from $f_{resonant}$ and $f_{half-BW}$ comprises calculating:

$$Q = \frac{f_{resonant}}{2 f_{half-BW}}.$$

6. The method of claim 1 wherein
    the distributed mass and spring device comprises a sample tube;
    calculating viscosity comprises:
        calculating:

$$R_T = \frac{X}{Q}$$

where
    X is XL or XC,
    XL is a magnitude of an inductive element of an electrical analog of the sample tube, and
    XC is a magnitude of an capacitive element of an electrical analog of the sample tube;
calculating:
    $R_F = R_T - R_O$,
    where:
        $R_O$ is a previously-determined friction of the sample tube when it does not contain fluid; and
    calculating:

$$u = \frac{\pi D^4 R_F}{128 L}$$

where
    u is viscosity,
    D is the inside diameter of the sample tube, and
    L is the active length of the sample tube.

7. The method of claim 1 wherein adjusting the adjustable delay in the phase adjuster comprises increasing the adjustable delay and wherein the method further comprises
setting the adjustable delay in the phase adjuster to λ/2;
adjusting the adjustable delay in the phase adjuster away from λ/2 by decreasing the adjustable delay until the amplitude of the output of the $$\text{receiver} = \frac{\sqrt{2}}{2}$$

times $A_{resonant}$ and, in response, measuring the frequency of the output of the receiver, $f_{High}$; and
calculating Q from $f_{resonant}$ and $f_{High}$.

8. The method of claim 7 wherein Q is calculated using the following equation:

$$Q = \frac{f_{resonant}}{f_{High} - f_{resonant}}.$$

9. An apparatus comprising:
components connected in a closed loop, the components including:
a distributed mass and spring device,
a transmitter coupled to the distributed mass and spring device to stimulate the distributed mass and spring device to vibrate,
a receiver coupled to the distributed mass and spring device to detect vibrations in the distributed mass and spring device containing a fluid,
an inverter, and
a phase adjuster comprising an adjustable delay;
a controller to:
cause the transmitter to stimulate the distributed mass and spring device to vibrate at a resonant frequency, $f_{resonant}$, of the distributed mass and spring device, $f_{resonant}$ having a wavelength λ,
set the adjustable delay in the phase adjuster to λ/2,
measure the amplitude of the output of the receiver, $A_{resonant}$, when the distributed mass and spring device is vibrating at $f_{resonant}$,
adjust the adjustable delay in the phase adjuster away from λ/2 until the amplitude of the output of the $$\text{receiver} = \frac{\sqrt{2}}{2}$$

times $A_{resonant}$ and, in response, measuring the frequency of the output of the receiver, $f_{half-BW}$; and
a processor to:
calculate Q from $f_{resonant}$ and $f_{half-BW}$, and
calculate a viscosity from Q.

10. The apparatus of claim 9 wherein:
an input of the inverter is connected to an output of the receiver;
an input of the phase adjuster is connected to an output of the inverter; and
an output of the phase adjuster is connected to an input of the transmitter.

11. An apparatus comprising:
components connected in a closed loop, the components including:
a distributed mass and spring device,
a transmitter coupled to the distributed mass and spring device to stimulate the distributed mass and spring device to vibrate, a receiver coupled to the distributed mass and spring device to detect vibrations in the distributed mass and spring device containing a fluid,
an inverter, and
a phase adjuster comprising an adjustable delay;
a controller to:
cause the transmitter to stimulate the distributed mass and spring device to vibrate at a resonant frequency, $f_{resonant}$, of the distributed mass and spring device, $f_{resonant}$ having a wavelength λ,
set the adjustable delay in the phase adjuster to λ/2,
measure the amplitude of the output of the receiver, $A_{resonant}$, when the distributed mass and spring device is vibrating at $f_{resonant}$,
adjust the adjustable delay in the phase adjuster away from λ/2 until the amplitude of the output of the $$\text{receiver} = \frac{\sqrt{2}}{2}$$

times $A_{resonant}$ and, in response, measuring the frequency of the output of the receiver, $f_{half-BW}$; and
a non-transitory computer-readable medium on which is recorded a computer program, the computer program comprising executable instructions, that, when executed, perform a method including:
calculating Q from $f_{resonant}$ and $f_{half-BW}$, and
calculating a viscosity from Q.

12. The apparatus of claim 11 wherein calculating Q from $f_{resonant}$ and $f_{half-BW}$ comprises calculating:

$$Q = \frac{f_{resonant}}{2 f_{half-BW}}.$$

13. The apparatus of claim 11 wherein calculating Q comprises calculating:

$$Q = \frac{f_{resonant}}{2 f_{half-BW}}.$$

* * * * *